(12) United States Patent
Kashiwagi et al.

(10) Patent No.: US 6,463,784 B2
(45) Date of Patent: Oct. 15, 2002

(54) MEASURING APPARATUS OF SLIDING FRICTION COEFFICIENT FOR VEHICLE RUNNING ROAD SURFACE

(75) Inventors: Akira Kashiwagi; Koichi Takagi, both of Chiba (JP)

(73) Assignee: Daiwa Manufacturing Co., Ltd., Chiba (JP)

( * ) Notice: Subject to any disclaimer, the term of this patent is extended or adjusted under 35 U.S.C. 154(b) by 0 days.

(21) Appl. No.: 09/815,119

(22) Filed: Mar. 22, 2001

(65) Prior Publication Data

US 2002/0046594 A1 Apr. 25, 2002

(30) Foreign Application Priority Data

Oct. 19, 2000  (JP) ........................................ 2000-319679

(51) Int. Cl.[7] ............................................... G01N 19/02
(52) U.S. Cl. ............................................................. 73/9
(58) Field of Search .................... 73/9, 10, 128–131, 73/146

(56) References Cited

U.S. PATENT DOCUMENTS

| 4,909,073 A | * | 3/1990 | Takahashi et al. ................ 73/9 |
| 4,958,512 A | * | 9/1990 | Johnsen ............................ 73/9 |
| 5,900,531 A | * | 5/1999 | Mani et al. ....................... 73/9 |

* cited by examiner

Primary Examiner—Robert Raevis
(74) Attorney, Agent, or Firm—Rodman & Rodman

(57) ABSTRACT

A measuring apparatus of sliding friction coefficient for vehicle running road surface includes a measuring wheel (4) supported rotatably on a support frame (10) and a brake unit (22) for braking said measuring wheel (4). A load cell (2) is disposed on the support frame (10) horizontal to a rotating shaft (19) of the measuring wheel (4) for measuring a tension yielded between the support frame (10) and the measuring wheel (4) by braking the measuring wheel (4), and a load cell (11) is disposed on the support frame (10) vertical to the rotating shaft (19) of the measuring wheel (4) for measuring a carrying weight loaded on the measuring wheel (4). The support frame (10) is arranged elevatably in the inside of a box-like casing (5).

8 Claims, 3 Drawing Sheets

MEASURING APPARATUS OF SLIDING FRICTION COEFFICIENT FOR VEHICLE RUNNING ROAD SURFACE

BACKGROUND OF THE INVENTION

1. Technical Field

The present invention relates to a measuring apparatus of sliding friction coefficient for vehicle running road surface and more particularly to a measuring apparatus for measuring a sliding friction coefficient for the purpose of establishing a traffic regulation to restrict the running speed of a vehicle running on snowy and/or frozen road surface as well as to make it compulsory to get the vehicle's wheels fitted with snow chains to prevent traffic accidents caused from the snowy and/or frozen road surface in the winter period.

2. Prior Art

In the known measuring apparatus of this kind, there are such apparatus for measuring sliding friction coefficient of road surface as installed directly on the road surface, as coupled to and towed by a normal automobile, and as operated during an automobile's running with a measuring apparatus loaded on the automobile.

While the known apparatus as described above installed directly on the road surface is compact and convenient for transporting, it is necessary to restrict or interrupt vehicle traffic and the like at the time of installing the apparatus and actually measuring, and consequently traffic congestion is created on the road especially where there is a lot of automobile traffic. The measuring apparatus towed by an automobile, on the other hand, can measure the friction coefficient during the automobile's running and does not restrict or interrupt traffic at the time of measuring, but it is a problem that the size of apparatus is made comparatively larger, and that it requires a comparatively large space for storage when not in use, as this is a type of measuring apparatus which is coupled to and towed by an automobile. Such measuring apparatus for loading on the automobile has been developed to measure the sliding friction coefficient mainly for a rapid transit high-way. The automobile upon which the measuring apparatus is loaded is limited to relatively larger sizes such as a large bus or truck, because the automobile has to be run at a high speed and bear the heavy weight load of the measuring apparatus. Consequently it is very expensive and uneconomical for manufacturing a vehicle suitable therefor or remodeling an existing vehicle properly.

SUMMARY OF THE INVENTION

An object of the present invention is to resolve the problems of the prior art as described above and to provide a measuring apparatus of sliding friction coefficient which is extremely compact in construction and can be simply, easily and removably loaded on a compact automobile, and which can measure simply and accurately the sliding friction on the running road surface during an automobile's running, without interrupting traffic of vehicles such as automobiles.

A measuring apparatus of sliding friction coefficient for vehicle running road surface according to the present invention comprises a measuring wheel supported rotatably on a support frame and a brake unit for braking the measuring wheel, wherein a load cell is provided on the support frame placed in the running direction of the measuring wheel horizontally to a rotating shaft thereof for measuring a tension between the support frame and the measuring wheel occurring from the braking action applied to the measuring wheel, a load cell for measuring a carrying weight loaded on the measuring wheel is provided on the support frame vertically to the rotating shaft of the measuring wheel, and the support frame of the measuring wheel is disposed for elevational movement within a box-like casing which is removably loaded on a compact automobile.

DETAILED DESCRIPTION OF THE PREFERRED EMBODIMENT

Figure 1:
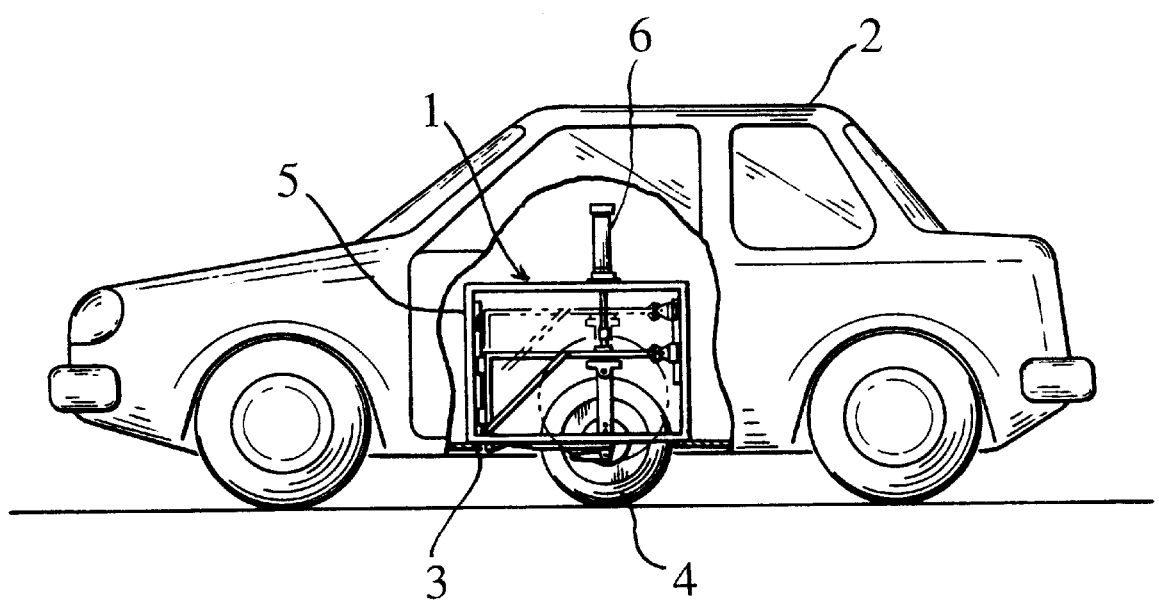
FIG. 1 is an elevation view showing the measuring apparatus of the present invention loaded on a vehicle.
Figure 2:
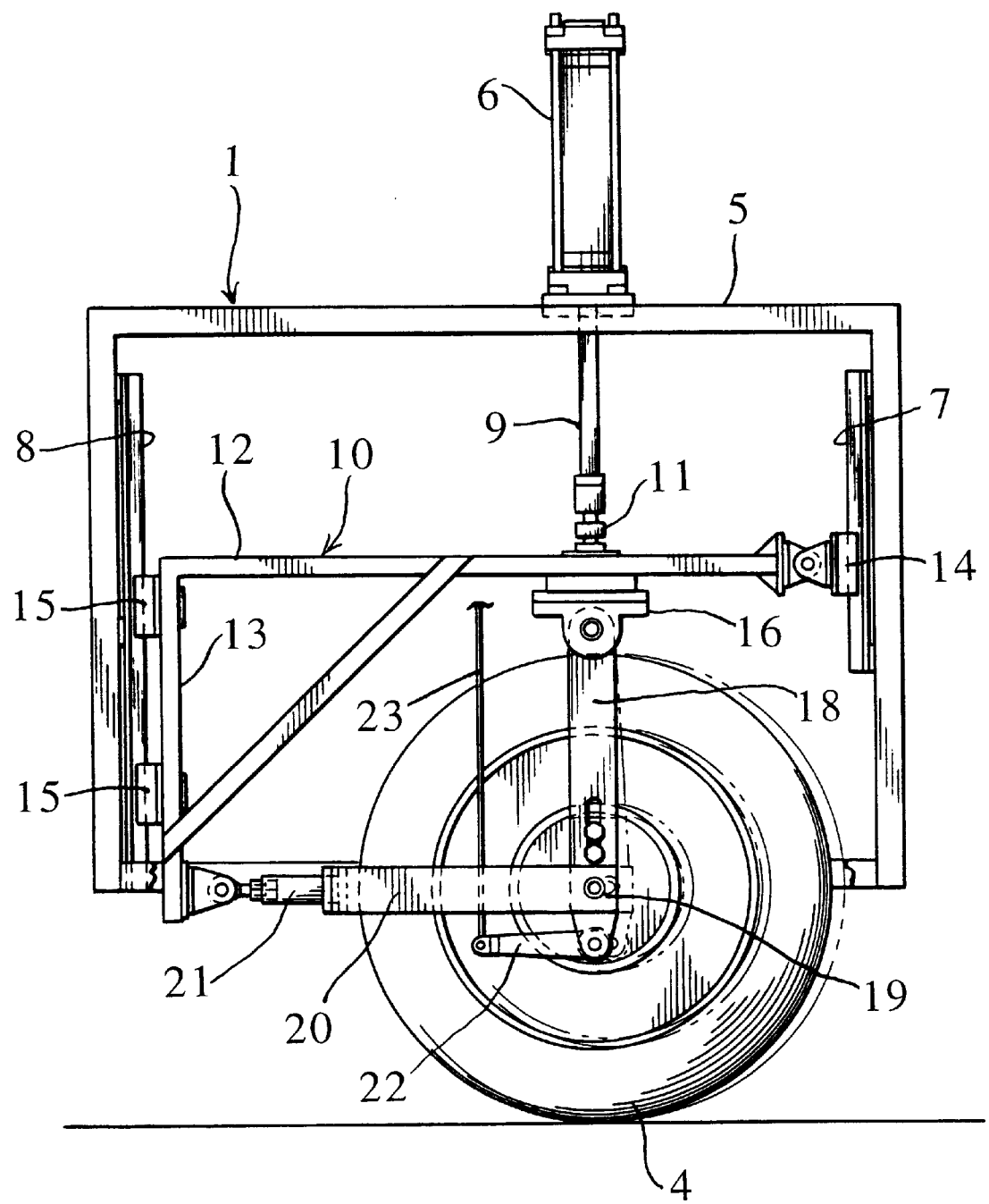
FIG. 2 is an elevation view of the measuring apparatus according to the present invention.
Figure 3:
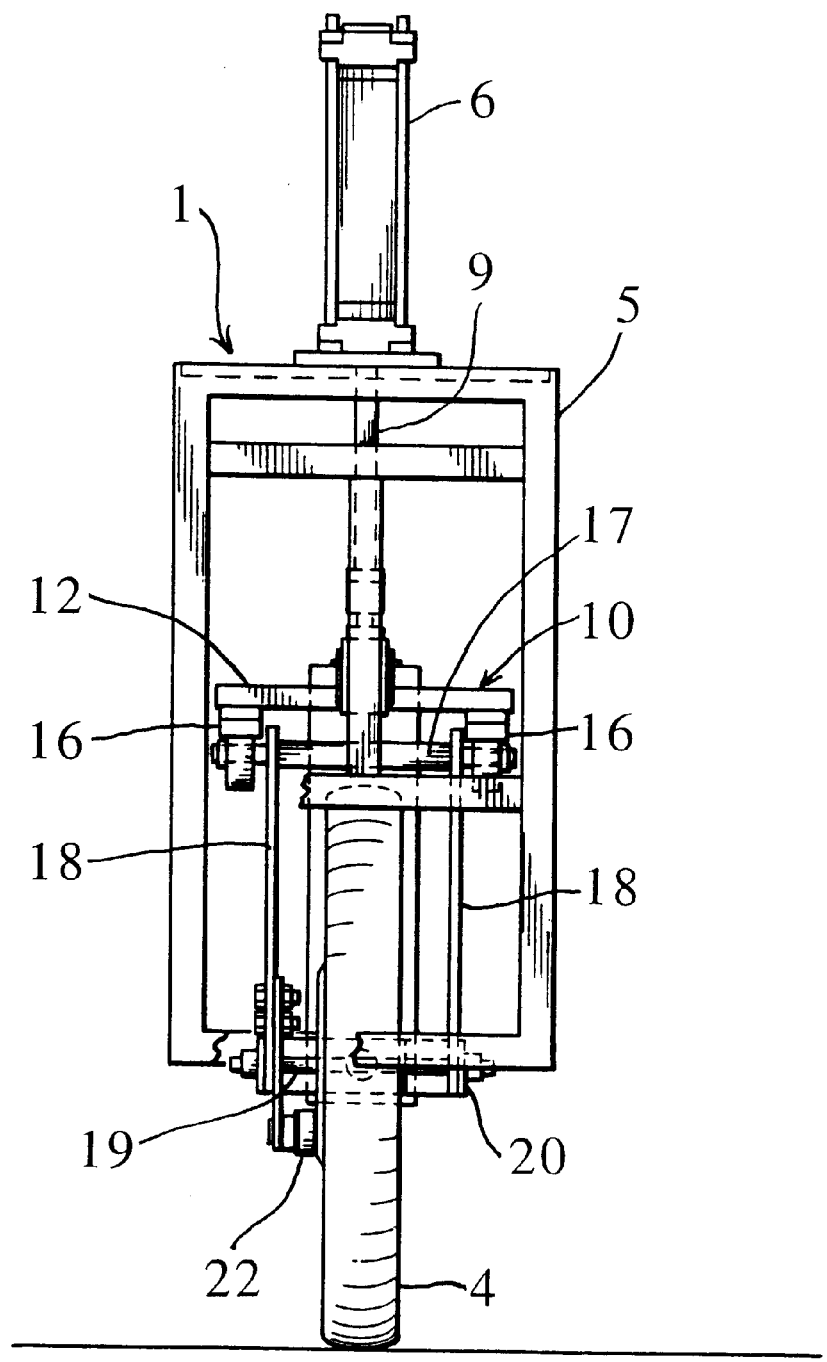
FIG. 3 is a side view of the measuring apparatus according to the present invention.

FIG. 1 shows a measuring apparatus 1 for measuring a sliding friction coefficient of the running road surface loaded on an automobile 2, said measuring apparatus 1 can be fixed on the floor chassis of the automobile 2 in such manner that a measuring wheel 4 can run in contact with the running road surface through an aperture 3 formed on the floor chassis of the automobile 2, and can be removed from the floor chassis of the automobile 2 for storage during non-use period outside of the winter period so that the automobile 2 can be used as a normal vehicle with the aperture 3 closed.

The measuring apparatus 1 includes a box-like casing 5 which is removably mounted on the floor chassis of the compact automobile 2. The casing 5 is opened at the bottom portion and is provided with an air cylinder 6 at the upper wall and with guide rails 7, 8 at the inside of the both side walls. A piston rod 9 of the air cylinder 6 is extended into the box-like casing 5 through an upper wall thereof and is fitted at the lower end to a support frame 10 disposed within the casing 5 via a load cell 11 for measuring a carrying weight to be loaded on the measuring wheel.

The support frame 10 comprises a horizontal plate 12 and a vertical plate 13 connected to one side of the horizontal plate 12. The horizontal plate 12 is provided at the other side with a slider 14 engaged with the guide rail 7 which is mounted on the box-like casing 5. The vertical plate 13 is arranged in the running direction of the running wheel 4, and is provided with sliders 15, 15 engaged to the guide rail 8 which is mounted on the box-like casing 5. Thus the support frame 10 can be elevated within the box-like casing 5 along the guide rails 7, 8 by means of the piston rod 9 of the air cylinder 6.

The horizontal plate 12 of the support frame 10 is provided at the both side ends of the lower face thereof with flanges 16, 16 projected downwardly. A support rod 17 is mounted between the flanges 16, 16 and is extended perpendicularly to the piston rod 9 in the lower side of the horizontal plate 12. Downwardly extending vertical arms 18, 18 are mounted pivotably on the support rod 17 near the flanges 16. The measuring wheel 4 is supported rotatably by a rotating shaft 19 between the lower ends of the two vertical arms 18, 18, which connect to one end of horizontal arms 20, 20 that extend horizontally to the running direction of the measuring wheel 4. The other end of the horizontal arms 20, 20 are connected to the lower end of the vertical plate 13 of the support frame 10 via a load cell 21. The load cell 21 measures a tension occurring between the support plate 10 and the measuring wheel 4 by braking the measuring wheel 4.

A brake unit 22 is mounted on one of the vertical arms 18 of the support frame 10 for braking the measuring wheel 4. The brake unit 22 is adapted to brake the measuring wheel 4 by actuating an air cylinder (not shown in the drawings) to pull a chain 23.

The support frame 10 of the measuring wheel 4 includes the vertical arms 18, 18 and horizontal arms 20, 20. As the load cell 11 is provided on the vertical arms 18, 18 extending perpendicularly to the rotating shaft 19 of the measuring wheel 4, a carrying weight loaded on the measuring wheel 4 can be measured accurately by the load cell 11. As the load cell 21 is provided on the horizontal arms 20, 20 extending horizontally to the rotating shaft 19 of the measuring wheel 4, a tension developed between the support frame 10 and the measuring wheel 4 by braking the measuring wheel 4 can be measured accurately by the load cell 21. The load cell 11 for measuring the carrying weight (i.e. the force in the vertical direction created in the air cylinder 6 by the upward and downward movements of the measuring wheel 4) and the load cell 21 for measuring the tension constitute a pressure gauge for calculating the sliding friction coefficient which is connected to a recorder.

The measuring wheel 4 must be driven by means of the air cylinder 6 to touch to the road surface with optional load during the running thereon at constant speed of an automobile equipped with the measuring apparatus according to the present invention. When the automobile with the measuring wheel 4 arrives at a measuring site having a snowy and/or frozen road surface, the measuring wheel is braked and stopped without changing the automobile's running speed, whereby a sliding friction is produced between the road surface and the measuring wheel 4. Then the tension corresponding to the sliding friction is developed between the support frame 10 and the measuring wheel 4. At this time, the carrying load is measured by the load cell 11 on the one hand and the tension is measured by the load cell 21 on the other hand. Then the friction coefficient can be obtained from the carrying load and tension load measured by the two load cells 11, 21.

The measuring apparatus of sliding friction coefficient for vehicle running road surface according to the present invention is extremely simple and compact in construction, and is simply and easily loadable on a compact automobile. Further, it is possible for the measuring apparatus of the present invention to perform the most accurate measuring of the sliding friction coefficient of the snowy and/or frozen road surface under the running of automobile without causing any interruption of vehicle traffic. Furthermore the measuring apparatus of the present invention is simply and easily removable from the automobile and is easy to store when not in use, during which time the automobile can be used as normal vehicle.

What is claimed is:

1. A measuring apparatus of sliding friction coefficient for vehicle running road surface comprising a support frame, a measuring wheel rotatably supported in said support frame, a brake unit on said support frame for braking said measuring wheel, a first load cell on said support frame for measuring tension between said support frame and said measuring wheel upon braking of said measuring wheel, a second load cell on said support frame for measuring a carrying weight loaded on said measuring wheel, and a box-like casing for said support frame having means for raising and lowering the support frame relative to the box-like casing, and wherein said support frame comprises a horizontal plate and a vertical plate connected to the horizontal plate, said horizontal plate having a bottom side with depending flanges and a support rod supported by the depending flanges, two spaced vertical arms having upper end portions mounted pivotally to said support rod, said vertical arms having opposite lower end portions for rotatably supporting the measuring wheel, said measuring wheel including a rotatable shaft that is rotatably supported in the lower end portions of the vertical arms, and said support frame further includes horizontal arms that each have one horizontal end portion connected to a respective said lower end portion of said vertical arms, and an opposite horizontal end portion connected to the vertical plate via the first load cell for measuring tension between the support frame and the measuring wheel.

2. A measuring apparatus according to claim 1 wherein said box-like casing has an upper wall provided with an air cylinder, said box-like casing further including opposite sidewalls provided with guide rails, said air cylinder includes a piston rod mounted via the second load cell to the support frame for measuring the carrying load, said box-like casing being provided with guide rails and said support frame being provided with sliders engaged to said guide rails such that said support frame is movable upwardly and downwardly along the guide rails in response to protraction and retraction of the piston rod by the air cylinder.

3. A measuring apparatus according to claim 2 wherein said box-like casing is detachably secured to the floor chassis of a motor vehicle through an aperture formed in the floor chassis of the motor vehicle such that the measuring wheel can run in contact with the running road surface.

4. A measuring apparatus according to claim 1 wherein said box-like casing is detachably secured to the floor chassis of a motor vehicle through an aperture formed in the floor chassis of the motor vehicle such that the measuring wheel can run in contact with the running road surface.

5. A measuring apparatus of sliding friction coefficient for vehicle running road surface comprising, a box-like casing for detachable securement to the floor chassis of a motor vehicle, said box-like casing having an upper wall and a pair of opposite side walls depending from the upper wall, an air cylinder being provided on the upper wall, said air cylinder having a piston rod that is extendible below said upper wall, said opposite side walls being provided with guide rails extending from an upper portion of the opposite side walls to a lower portion of the opposite side walls, a support frame provided between said opposite side walls, said support frame having at least one slider engaged with each of the respective said guide rails of said box-like casing for slidable movement of the support frame on said guide rails, said support frame being connected to and supported by the piston rod of the air cylinder for slidable movement of said support frame between the opposite side walls of the box-like casing such that the support frame is moveable downwardly and upwardly between the opposite side walls along the guide rails upon operation of the air cylinder to protract and retract the piston rod relative to the upper wall of the box-like casing, a measuring wheel supported for rotation on a rotating shaft in said support frame and movable together with said support frame in the upward and downward directions, a brake unit provided on the support frame for braking said measuring wheel, a first load cell provided on the piston rod of the air cylinder and mounted to the support frame vertically of the rotating shaft of the measuring wheel for measuring a vertical force load on the measuring wheel, and a second load cell disposed on the support frame along a line that is perpendicular to said rotation shaft and perpendicular to the direction of downward and upward movement of said piston rod, for measuring a tension between the support frame and the measuring wheel when the measuring wheel is being subject to braking.

6. A measuring apparatus according to claim 5 wherein said piston rod of the air cylinder is mounted through the first load cell to the upper wall of the box-like casing for measuring the vertical force to the support frame vertically of the rotating shaft of the measuring wheel.

7. A measuring apparatus according to claim 6 wherein said support frame comprises a horizontal plate and a vertical plate connected to said horizontal plate, said horizontal plate has a bottom side with depending flanges and a support rod supported by the depending flanges, said support rod being provided with two spaced depending arms having lower end portions, said rotating shaft of said measuring wheel being supported at respective said lower end portions of said depending arms, a pair of horizontal arms, each said horizontal arm having one end portion connected to a respective said lower end portion of said depending arms, each said horizontal arm having an opposite end portion connected to the vertical plate through the second load cell for measuring the tension.

8. A measuring apparatus according to claim 5 wherein said support frame comprises a horizontal plate and a vertical plate connected to said horizontal plate, said horizontal plate has a bottom side with depending flanges and a support rod supported by the depending flanges, said support rod being provided with two spaced depending arms having lower end portions, said rotating shaft of said measuring wheel being supported at respective said lower end portions of said depending arms, a pair of horizontal arms, each said horizontal arm having one end portion connected to a respective said lower end portion of said depending arms, each said horizontal arm having an opposite end portion connected to the vertical plate through the second load cell for measuring the tension.

* * * * *